United States Patent
Gill

(10) Patent No.: US 11,306,012 B2
(45) Date of Patent: Apr. 19, 2022

(54) SOIL-BASED FLOW-THROUGH RHIZOSPHERE SYSTEM FOR TREATMENT OF CONTAMINATED WATER AND SOIL

(71) Applicant: Reed Scientific Services Ltd., Vancouver (CA)

(72) Inventor: Lucian Stephen Gill, South Yorkshire (GB)

(73) Assignee: Reed Scientific Services Ltd., Vancouver (CA)

( * ) Notice: Subject to any disclaimer, the term of this patent is extended or adjusted under 35 U.S.C. 154(b) by 0 days.

(21) Appl. No.: 16/490,735

(22) PCT Filed: Dec. 6, 2018

(86) PCT No.: PCT/CA2018/051563
§ 371 (c)(1),
(2) Date: Sep. 3, 2019

(87) PCT Pub. No.: WO2019/134028
PCT Pub. Date: Jul. 11, 2019

(65) Prior Publication Data
US 2020/0002203 A1  Jan. 2, 2020

Related U.S. Application Data

(60) Provisional application No. 62/612,929, filed on Jan. 2, 2018.

(51) Int. Cl.
*C02F 3/34* (2006.01)
*B09C 1/10* (2006.01)
(Continued)

(52) U.S. Cl.
CPC ............... *C02F 3/34* (2013.01); *B09C 1/10* (2013.01); *B09C 1/105* (2013.01); *C02F 3/327* (2013.01);
(Continued)

(58) Field of Classification Search
CPC .. C05F 11/08; C05F 17/20; C02F 3/34; C02F 3/046; B09C 1/10; C12N 1/20
(Continued)

(56) References Cited

U.S. PATENT DOCUMENTS 4,793,929 A  12/1988  Kickuth et al.
4,855,040 A   8/1989  Kickuth
(Continued)

FOREIGN PATENT DOCUMENTS

CN  102757132   1/2014
CN  104974960  10/2015
(Continued)

OTHER PUBLICATIONS

International Search Report and Written Opinion dated Feb. 22, 2019 in PCT/CA2018/051563.
(Continued)

*Primary Examiner* — Claire A Norris
(74) *Attorney, Agent, or Firm* — Stradley Ronon Stevens & Young, LLP

(57) ABSTRACT

A process for constructing a soil-based rhizosphere flow-through system to break down contaminants in contaminated water. The process includes the steps of: providing plants planted in soil in a test bioreactor, the plants providing a rhizosphere; exposing the rhizosphere to the contaminated water; extracting microorganisms from the rhizosphere following their exposure to the contaminated water; preparing a microbial suspension from the extract; subjecting the microbial suspension to growth conditions to increase the concentration of the microorganisms, thereby preparing a soil conditioner; adding the soil conditioner to soil in a contained area having a water flow inlet and outlet; and planting a plurality of plants in the soil, the plants being of the same species as the plants of the test bioreactor.

27 Claims, 7 Drawing Sheets

(51) Int. Cl.
*C02F 3/32* (2006.01)
*C09K 17/00* (2006.01)
*C12N 1/20* (2006.01)
*C02F 101/36* (2006.01)
*C02F 103/06* (2006.01)

(52) U.S. Cl.
CPC ............... *C09K 17/00* (2013.01); *C12N 1/20* (2013.01); *C02F 2101/36* (2013.01); *C02F 2103/06* (2013.01)

(58) Field of Classification Search
USPC ................................. 210/602, 601
See application file for complete search history.

(56) References Cited

U.S. PATENT DOCUMENTS

| | | | |
|---|---|---|---|
| 4,904,386 A | 2/1990 | Kickuth | |
| 5,078,881 A * | 1/1992 | Augustine | B01D 53/84 210/602 |
| 5,273,653 A | 12/1993 | Kickuth | |
| 5,458,747 A | 10/1995 | Marks et al. | |
| 5,637,218 A | 6/1997 | Kickuth | |
| 6,200,469 B1 | 3/2001 | Wallace | |
| 6,406,627 B1 | 6/2002 | Wallace | |
| 6,576,130 B2 | 6/2003 | Wallace | |
| 6,599,423 B2 | 7/2003 | Boles et al. | |
| 6,652,743 B2 | 11/2003 | Wallace et al. | |
| 7,718,063 B2 * | 5/2010 | Jacquet | B09C 1/105 210/602 |
| 8,420,362 B2 | 4/2013 | Crawford et al. | |
| 8,696,907 B2 | 4/2014 | Rausch et al. | |
| 9,034,633 B2 | 5/2015 | Kumar et al. | |

FOREIGN PATENT DOCUMENTS

| | | |
|---|---|---|
| JP | 11090411 | 4/1996 |
| JP | 2000312582 | 11/2000 |
| JP | 3618785 | 2/2005 |
| JP | 2007160209 | 6/2007 |
| JP | 2009154044 | 7/2009 |
| JP | 201184449 | 4/2011 |
| WO | 2017034827 | 3/2017 |

OTHER PUBLICATIONS

Yadab et al., "Remediation of LNAPL Contaminated Groundwater Using Plant-Assisted Biostimulation and Bioaugmentation Methods", 2014, Water Air Soil Pollut, 225, pp. 1793-1799.

Kadlec et al., "Treatment Wetlands", 2009, CRC Press Taylor and Francis Group, Boca Raton.

* cited by examiner

SOIL-BASED FLOW-THROUGH RHIZOSPHERE SYSTEM FOR TREATMENT OF CONTAMINATED WATER AND SOIL

FIELD OF THE INVENTION

The invention relates to treatment of contaminated water and more specifically to systems for treating contaminated water and soil using processes based on soil-based rhizosphere flow-through systems. Processes for construction of the systems and implementation of the processes are described.

BACKGROUND

The breakdown of organic chemical contaminants (also known as "recalcitrants") in wastewater and in soil is a widely known problem. Mechanical treatment systems are generally not very effective at breaking down organic chemical contaminants and even when they are used, they are energy intensive, require rigorous maintenance and have high operating costs.

Systems known as "constructed wetlands" are a type of reed bed technology based on reeds planted in gravel substrates. Such constructed wetlands cannot provide treatment of contaminated water with high concentrations of contaminant compounds and as such, tend to be limited to treatment of effluents with low loads of contaminants and/or effluents with chemically simple contaminants. In instances where constructed wetlands are employed for less problematic organic contaminants, the treatment systems generally have a limited operational lifetime due to the buildup of sediment and/or precipitates. The impenetrable nature of the gravel based media limits the positive effect that rhizome regeneration can have on the sediments and precipitates, preventing continual mixing and interaction of the soil with the plant matrix. As such, the hydraulic conductivity on constructed wetlands is significantly reduced after a period of approximately 8-12 years at which point, the gravel substrate requires refurbishment or replacement. Additional stages to constructed wetland treatment systems have been incorporated at the front and/or back end of these treatment systems. These "bolt-on" solutions have included installation of a charcoal filter at the front and/or back end of the treatment system. The charcoal filtration unit allows for adsorption of the contaminants onto charcoal. Such a filter must be removed and replaced periodically and disposed of into a landfill. Another modification has been incorporation of forced aeration solutions within a constructed wetland design so as to increase the oxygenation of the effluent.

These modifications to constructed wetlands have been able to achieve the required chemical loading reductions. However, they are far from best practice solutions. Removal of filtration units and disposal into landfill is an unnecessary operating cost and is to the detriment of the environment. Ultimately this method is removal, and not treatment (i.e. breakdown and/or mineralization into harmless substances). The disposal of this waste into landfill goes against the sustainability criteria claimed by such constructed wetland systems. The use of forced aeration systems within a constructed wetland ultimately is the creation of a mechanical/biological hybrid treatment system. The use of mechanical methods to increase treatment capabilities is also to the detriment of capital and operating expenditures and the sustainability criteria claimed by constructed wetland systems.

Conventional soil-based reed bed systems do not have the same issues with blockage which occur in constructed wetlands. The soil substrate promotes rhizome regeneration, therefore allowing sediments and precipitates to be amalgamated and integrated into the soil. Hydraulic pathways are continually renewed and therefore soil-based reed bed systems do not require refurbishment or replacement.

Early efforts to adapt reed beds for treating water containing organic contaminants conducted by Reinhold Kickuth are described in U.S. Pat. Nos. 5,637,218, 5,273,653, 4,904,386, 4,855,040, and 4,793,929, each of which is incorporated herein by reference in its entirety. Additional efforts relating to mechanical aspects of moving water through wetland cell systems are described in U.S. Pat. Nos. 6,652,743, 6,576,130, 6,406,627 and 6,200,469, each of which is incorporated herein by reference in its entirety.

JP 3618785, incorporated herein by reference in its entirety, describes a method for cleaning contaminated soil using crushed cell bodies of microorganisms that have enzymes capable of decomposing contaminants. Preferred microorganisms are pseudomonads of specific species and strains. Decontamination of volatile organic chlorine compounds such as trichloroethylene is described.

JP 11090411A, incorporated herein by reference in its entirety, describes a method for decomposing contaminants in soil or ground water, particularly aromatic compounds such as creosole, trichloroethylene, and dichloroethylene using a contaminant decomposing microorganism which is cultured in a culture medium which includes elements of the contaminated environment.

JP 2000312582A, incorporated herein by reference in its entirety, describes a microorganism capable of decomposing cyanide compounds which are useful for treating soil, wastewater or underground water contaminated with cyanide compounds. The microorganisms are of the genus *Cordona* and the genus *Burkholderia*.

JP 2007160209A, incorporated herein by reference in its entirety, describes a method for improving water quality which includes collection of soil containing a plurality of microorganisms contaminated by sewage, separating the microorganisms and identifying them in a purification process and supporting them on a porous carrier material in a sewage treatment system.

JP 2009154044A, incorporated herein by reference in its entirety, describes a method for purifying contaminated soil using microorganisms having the ability to degrade the contaminant (such as hydrocarbons, organic chlorine containing compounds and cyanide compounds). The soil is sampled and tested to evaluate the applicability of bioremediation. The soil is combined with the microorganisms in a soil molded body which is charged into a well at the upstream end of a groundwater stream flowing through the contaminated soil area.

JP 2011084449A, incorporated herein by reference in its entirety, describes materials and methods for improving degraded and contaminated soil and accelerating cleaning of water. Selected microorganisms are cultured in a residual liquid after starch and gluten are extracted from wheat or grain. This material is used in a number of applications, including use as a waste treatment agent.

U.S. Pat. No. 5,078,881, incorporated herein by reference in its entirety, describes a method for decontaminating solutions containing wastes (typically pesticides) in a soil bed reactor using a sample tank and a holding tank which is aerated. Water from the holding tank is applied to the upper soil surface of the soil bed reactor. Microbial action in the soil degrades the toxic materials.

U.S. Pat. No. 5,458,747, incorporated herein by reference in its entirety, describes a process for in situ bio-electrokinetic remediation of contaminated soil containing hazardous mixed wastes as organic pollutants and hazardous heavy metals. Bioremediation of the organic pollutants is followed by removal of the hazardous material. Cultured microorganisms, nutrients and growth factors are added to clean soil adjacent to contaminated soil prior to initiating the bio-electrokinetic process.

U.S. Pat. No. 6,599,423, incorporated herein by reference in its entirety, describes processes for destruction of air, water, and soil contaminants (especially volatile organic compounds and chloroethylenes, and particularly trichloroethylene) using naturally occurring microorganisms. The processes may be applied on a batch or continuous basis to contaminated soil and groundwater, to contaminated effluents from industrial operations. In one example, a procedure for obtaining a purified culture of microorganisms useful in accordance with the present invention comprises the steps of: (1) collecting a sample of material from the site contaminated with obnoxious chemicals; (2) enriching the microorganisms found living in the sample; (3) separating the strains of microorganisms capable of having different metabolisms for the various chemicals in the sample from the site, from each other; (4) purifying the strains which are capable of biodegrading the chemicals to be disposed of; (5) applying the strain to the locus of the contaminants to be disposed of; and (6) monitoring of removal of the contaminants.

U.S. Pat. No. 8,420,362, incorporated herein by reference in its entirety, describes a method for increasing the concentration of calcium carbonate in a geomaterial that contains indigenous microorganisms capable of hydrolyzing urea to ammonia. The method includes enriching the geomaterial with a source of nutrients, adding urea to the geomaterial which is hydrolyzed to ammonia and which raises the pH of the geomaterial, and adding a source of calcium ions to the geomaterial. Carbonate ions obtained by the hydrolysis of the urea combine with calcium ions to form calcium carbonate.

U.S. Pat. No. 9,034,633, incorporated herein by reference in its entirety, describes a biopile-based bioremediation method for treatment of hydrocarbon waste with high aromatic content. A bio-pile is a bioremediation technology in which excavated soils are mixed with soil amendments, formed into compost piles, and enclosed for treatment. The basic bio-pile system includes a treatment bed, an aeration system, an irrigation/nutrient system and a leachate collection system. It is indicated that the isolated microorganisms are adsorbed on a biodegradable carrier and acclimatized to grow in the presence of aromatic hydrocarbon waste by adding samples of the contaminated soil or waste.

U.S. Pat. No. 8,696,907, incorporated herein by reference in its entirety, describes a plant and a method for the treatment and disposal of waste water containing salts and oil, in particular produced water, comprising at least one settling area for receiving the waste water and for separating oil proportions from the waste water, at least one subsequent reed bed area having plants for the uptake and degradation of contaminants in the waste water, at least one modular basin area having a plurality of utility basins, whereby a utility basin, controlled by way of distribution means, can be supplied with treated waste water from the reed bed area and/or from at least one other utility basin, and at least one saline area for the reception of the residual water from the modular basin area and for the evaporation of water and the concentration of salt.

WO 2017/034827, incorporated herein by reference in its entirety, describes a method for increasing the concentration of metal carbonates in a heavy metal contaminated geomaterial utilizing indigenous ureolytic microorganisms. The method may be used for bioremediation of heavy metal contaminated geomaterials. There is description of addition of nutrients such as molasses to encourage growth of microorganisms.

The contaminants in soil tend to move under the impact of rainfall and groundwater and are then defined as pollution. Where rainfall carries the pollution downwards into the underlying strata, possibly an aquifer, then some type of "pump and treat" or microbiological injection is required to deal with pollution usually defined as a "plume".

For the surface and near surface material there exists expensive systems such as thermal desorption or excavation to landfill. However increasingly the application of microbiology is being used to decontaminate such soil. This technique is usually applied with limited mechanical application such as light ploughing or aggregating the soil into a "biopile."

The first stage in this process is quite costly however since it generally involves extraction of samples of the contaminated soil and determination and isolation of any in situ bacteria. The isolated bacterial population is then released against the contaminants to establish the efficiency of the isolate and then a fermentation process is carried out to increase the bacterial species concentrations. In many cases however, although the target chemical is broken down, the products of this action may be byproducts which are equally as toxic as the parent. The process itself stops at less than 100% removal because these byproducts become toxic to the bacteria carrying out the initial degradation.

A need exists to improve soil-based reed-bed systems for more effective treatment of water and soil containing organic contaminants.

SUMMARY

One aspect of the invention is a process for preparing a soil conditioner to increase the rate of decontamination of contaminated water or contaminated soil, the process comprising: a) providing a rhizosphere; b) exposing the rhizosphere to the contaminated water; extracting microorganisms from the rhizosphere after step b); c) preparing a microbial suspension from the extract; and d) subjecting the microbial suspension to growth conditions to increase the concentration of the microorganisms, thereby preparing the soil conditioner.

In some embodiments of the process for preparing a soil conditioner, step b) comprises generating a flow of the contaminated water across the rhizosphere, the flow entering at an inlet and exiting at an outlet.

In some embodiments of the process for preparing a soil conditioner, the flow of the contaminated water is conducted for a period of about 4 to about 8 weeks.

In some embodiments of the process for preparing a soil conditioner, the process further comprises testing of outflow from the outlet to identify one or more metabolic products of one or more contaminants present in the contaminated water.

In some embodiments of the process for preparing a soil conditioner, the process further comprises measuring the amount of microorganisms present in the extract in the microbial suspension.

In some embodiments of the process for preparing a soil conditioner, the process further comprises measuring the amount of microorganisms present in the soil conditioner, wherein a plate count of at least about 106 counts/mL indicates that the soil conditioner is suitable for use in treatment of a soil bed in construction of the soil-based flow-through rhizosphere system.

In some embodiments of the process for preparing a soil conditioner, the rhizosphere is of a wetland plant.

In some embodiments of the process for preparing a soil conditioner, the wetland plant is selected from the group consisting of *Phragmites australis, Arundo donax* L., *Neyraudia reynaudiana, Phalaris arundinacea, Glyceria maxima, Elegia tectorum, Thamnochortus insignis*, a species of the genus *Calamagrostis*, a species of the genus *Sparganium*, and a species of the genus *Typha*.

In some embodiments of the process for preparing a soil conditioner, steps a) and b) are conducted in a test bioreactor having a volume of about 10 L to about 50 L.

In some embodiments of the process for preparing a soil conditioner, the contaminated water comprises organic contaminants.

In some embodiments of the process for preparing a soil conditioner, the microbial suspension comprises microorganisms originally present in the contaminated water and microorganisms originally present in the rhizosphere.

Another aspect of the invention is a process for constructing a soil-based rhizosphere flow-through system to break down contaminants in contaminated water, the process comprising: a) providing plants planted in soil in a test bioreactor, the plants providing a rhizosphere; b) exposing the rhizosphere to the contaminated water; c) extracting microorganisms from the rhizosphere after step b); d) preparing a microbial suspension from the extract; e) subjecting the microbial suspension to growth conditions to increase the concentration of the microorganisms, thereby preparing a soil conditioner; f) adding the soil conditioner to soil in a contained area having a water flow inlet and outlet; and g) planting a plurality of plants in the soil, the plants being of the same species as the plants of step a).

In some embodiments of the process for constructing a soil-based rhizosphere flow-through system, step b) comprises generating a flow of the contaminated water across the rhizosphere, the flow entering at an inlet and exiting at an outlet.

In some embodiments of the process for constructing a soil-based rhizosphere flow-through system, the flow of the contaminated water is conducted for a period of about 4 to about 8 weeks.

In some embodiments of the process for constructing a soil-based rhizosphere flow-through system, the process further comprises testing of outflow from the outlet to identify one or more metabolic products of one or more contaminants present in the contaminated water.

In some embodiments of the process for constructing a soil-based rhizosphere flow-through system, the process further comprises measuring the amount of microorganisms present in the extract in the microbial suspension.

In some embodiments of the process for constructing a soil-based rhizosphere flow-through system, the process further comprises measuring the amount of microorganisms present in the soil conditioner, wherein a plate count of at least about 106 counts/mL indicates that the soil conditioner is suitable for use in treatment of a soil bed in construction of the soil-based flow-through rhizosphere system.

In some embodiments of the process for constructing a soil-based rhizosphere flow-through system, the rhizosphere is of a wetland plant.

In some embodiments of the process for constructing a soil-based rhizosphere flow-through system, the wetland plant is selected from the group consisting of *Phragmites australis, Arundo donax* L., *Neyraudia reynaudiana, Phalaris arundinacea, Glyceria maxima, Elegia tectorum, Thamnochortus insignis*, a species of the genus *Calamagrostis*, a species of the genus *Sparganium*, and a species of the genus *Typha*.

In some embodiments of the process for constructing a soil-based rhizosphere flow-through system, steps a) and b) are conducted in a test bioreactor having a volume of about 10 L to about 50 L.

In some embodiments of the process for constructing a soil-based rhizosphere flow-through system, the contaminated water comprises organic contaminants.

In some embodiments of the process for constructing a soil-based rhizosphere flow-through system, the microbial suspension comprises microorganisms originally present in the contaminated water and microorganisms originally present in the rhizosphere.

Another aspect of the invention is a soil-based flow-through rhizosphere system for breaking down contaminant organic compounds in contaminated water, the system comprising: a) a contained area comprising soil treated with a soil conditioner prepared according to the process described herein and planted with plants of the same species as the rhizosphere, the contained area having a water flow inlet and a flow outlet; b) a tank for holding the contaminated water before entry of the contaminated water into the contained area; the tank in flow communication with the flow inlet; and c) a retention pond in communication with the flow outlet.

In some embodiments, the soil-based flow-through rhizosphere system further comprises a soak-away discharge pond in flow communication with the retention pond to allow discharge of treated water into the environment.

In some embodiments, the soil-based flow-through rhizosphere system further comprises a recirculation line in flow communication between the retention pond and the water flow inlet.

In some embodiments of the soil-based flow-through rhizosphere system, the contained area is a container configured to provide predominately horizontal flow of the contaminated water from the flow inlet to the flow outlet.

In some embodiments of the soil-based flow-through rhizosphere system, the container comprises a soil depth of between about 0.4 m to about 0.5 m to provide a predominately aerobic soil environment.

In some embodiments of the soil-based flow-through rhizosphere system, the contained area is a container configured to provide predominately vertical flow of the contaminated water from the flow inlet to the flow outlet.

In some embodiments of the soil-based flow-through rhizosphere system, the container comprises a soil depth of between about 0.8 m to about 1.0 m to provide soil having both a predominately aerobic soil environment closer to the soil surface and a predominately anaerobic soil environment closer to the bottom of the container.

Another aspect of the invention is a process for breaking down contaminant compounds in contaminated soil, the process comprising: a) isolating contaminated water from the contaminated soil; b) providing a rhizosphere; c) exposing the rhizosphere to the contaminated water; d) extracting microorganisms from the rhizosphere after step e); preparing a microbial suspension from the extract; f) subjecting the microbial suspension to growth conditions to increase the concentration of the microorganisms, thereby preparing a soil conditioner; and g) treating the contaminated soil with the soil conditioner.

In some embodiments of the process for breaking down contaminant compounds in contaminated soil, step c) comprises generating a flow of the contaminated water across the rhizosphere, the flow entering at an inlet and exiting at an outlet.

In some embodiments of the process for breaking down contaminant compounds in contaminated soil, the flow of the contaminated water is conducted for a period of about 4 to about 8 weeks.

In some embodiments of the process for breaking down contaminant compounds in contaminated soil, the process further comprises testing of outflow from the outlet to identify one or more metabolic products of one or more contaminants present in the contaminated water.

In some embodiments of the process for breaking down contaminant compounds in contaminated soil, the process further comprises measuring the amount of microorganisms present in the extract in the microbial suspension.

In some embodiments of the process for breaking down contaminant compounds in contaminated soil, the process further comprises measuring the amount of microorganisms present in the soil conditioner, wherein a plate count of at least about 106 counts/mL indicates that the soil conditioner is suitable for use in treatment of the contaminated soil.

In some embodiments of the process for breaking down contaminant compounds in contaminated soil, the rhizome is of a wetland plant.

In some embodiments of the process for breaking down contaminant compounds in contaminated soil, the wetland plant is selected from the group consisting of *Phragmites australis, Arundo donax* L., *Neyraudia reynaudiana, Phalaris arundinacea, Glyceria maxima, Elegia tectorum, Thamnochortus insignis*, a species of the genus *Calamagrostis*, a species of the genus *Sparganium*, and a species of the genus *Typha*.

In some embodiments of the process for breaking down contaminant compounds in contaminated soil, step c) is conducted in a test bioreactor having a volume of about 10 L to about 50 L.

In some embodiments of the process for breaking down contaminant compounds in contaminated soil, the contaminated water comprises organic contaminants.

In some embodiments of the process for breaking down contaminant compounds in contaminated soil, the microbial suspension comprises microorganisms originally present in the contaminated soil and microorganisms originally present in the rhizosphere.

BRIEF DESCRIPTION OF THE DRAWINGS

Various objects, features and advantages of the invention will be apparent from the following description of particular embodiments of the invention, as illustrated in the accompanying drawings. The drawings are not necessarily to scale. Emphasis is instead placed upon illustrating the principles of various embodiments of the invention.

DETAILED DESCRIPTION

Rationale and Overview

Figure 1:
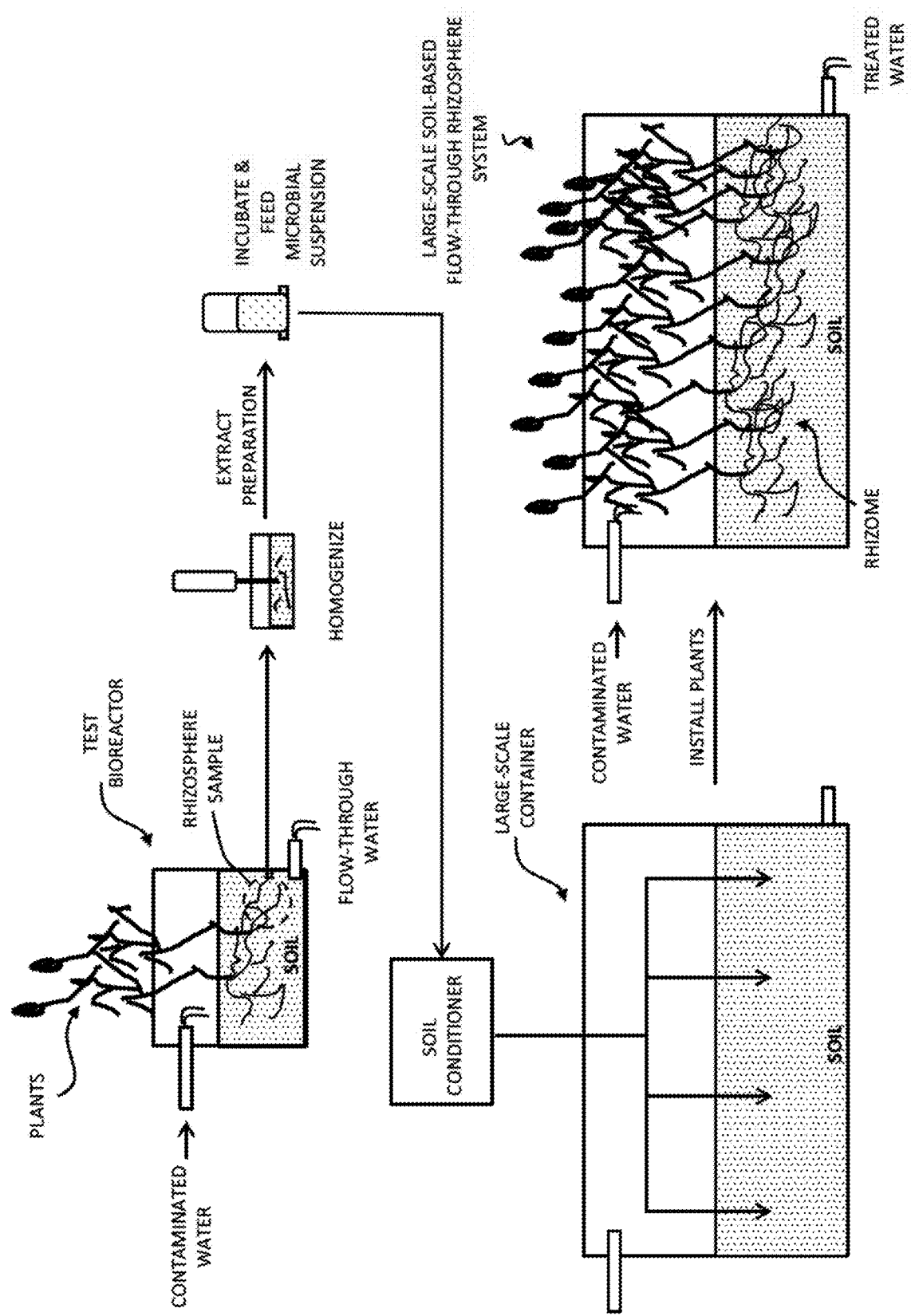
FIG. 1 is an illustration of an embodiment of a process for constructing a soil-based rhizosphere flow-through system.

The use of a soil substrate for a rhizosphere system rather than gravel provides distinct advantages over constructed wetlands in terms of treatment capacity. The present inventor has recognized that soil has a significantly larger surface area than gravel and that this extra surface area allows a significantly larger population of microorganisms to populate a soil-based substrate. A larger population of microorganisms is directly proportional to more effective treatment potential per unit of surface area of a treatment system. This gives a soil-based rhizosphere system greater treatment capacity.

A number of shortcomings of using soil-based rhizosphere systems to treat contaminated water have been recognized by the present inventor. One problem is the excessive length of time required to develop treatment capacity within a soil-based rhizosphere system. Another problem which occurs from time to time is poor reproducibility and a related inability to guarantee successful treatment. Simply relying upon the microbial ecology of the soil without enrichment is not sufficient to ensure that a given soil-based rhizosphere system will efficiently break down organic contaminants in water or in soil. It was recognized by the inventor that populations of bacteria present in both the rhizome itself and in contaminated water and/or soil can be induced to adapt to each other and speciate to improve the extent of decontamination. It was also recognized that such conditions should avoid exposing the rhizome and root structure to excessive levels of organic contaminants in order to avoid stressing or shock-loading the plants. It was further recognized that an establishment phase between commissioning of a soil-based reed bed system and full operation of the system would have the effect of limiting detrimental impacts on the plants and microbial populations in the soil and rhizome of the plants.

The microbial populations within a soil-based reed bed system include naturally occurring bacteria within the soil and the rhizome of the plant. This microbial population develops and speciates under the impact of the contaminated water added to the system. As such the microbial population becomes somewhat limited, thereby limiting the intensity of treatment.

Overcoming the aforementioned shortcomings of soil-based reed bed systems has until now required a number of possible strategies to minimize problems which may occur. Such strategies have included (i) incorporation of a long establishment phase to allow the microbial populations to develop; (ii) costly construction and operation of a pilot treatment system to confirm proof of operation; and (iii) restricting the application of soil-based reed bed systems to less chemically complex organic contaminants. In addition to these strategies, the risks accepted are that the desired treatment standards may not be achieved and that such failures may result in penalties against the technology provider.

With respect to treatment of contaminated soil using a biopile, two major problems exist. Firstly, a complex mixture of chemical pollutants, such as pesticides may, by acting synergistically, inhibit all bacterial activity such that the soil is biologically dead. This process is becoming apparent in soils that have pesticide, herbicide sprayed on them as part of the agricultural cycle with the decrease in soil organisms producing substantial drop in yield. The second case involves situations whereby a low level of microbiological activity is present but is suppressed by its own waste products (the breakdown products).

The complete removal of contaminants and the byproducts therefore requires a series of microbiological co-metabolic actions to occur to complete the degradation.

The present inventor has recognized that within nature, collections of organisms capable of providing such co-metabolic activity are present in the rhizospheres of certain classes of plants. The soil microorganisms act together to produce a multiplicity of reaction pathways. At its simplest, the catabolic and metabolic activity within the rhizosphere which breaks down fertilizer and other nutrients to synthesize plant tissue provides the soil domain necessary for a complex mixture of microorganisms to develop.

The present invention therefore relates to the methodology of using plant rhizosphere which has been created within a contaminated soil matrix thereby producing a consortium of bacteria and other soil microorganisms which are capable of completely degrading the contamination contained therein. This methodology produces a liquid extract herein referred to as "soil conditioner" which contains high levels of appropriate organisms which can be applied, for example by conventional methods such as simple spray techniques to the contaminated soil. The expensive steps of isolation, identification and fermentation of individual species and strains of microorganisms are not required and the resulting product overcomes the present deficiencies of conventional bioremediation techniques.

Various embodiments of the process described hereinbelow incorporate microorganisms present within the contaminated water or soil and the rhizome of the plant, as well as the soil containing the rhizome (which are collectively referred to as the "rhizosphere." These microorganisms are extracted, and subjected to growth conditions to increase their concentrations, thereby providing a soil conditioner. This soil-conditioner is added to the soil to increase the total metabolic activity provided by the microorganisms in development of a stabilized soil matrix for the rhizosphere to be used for degradation of organic contaminants in the contaminated water or in contaminated soil.

Definitions

As used herein, the terms "contaminated water" and "contaminated soil" refers to water containing any type of contaminant, in particular an organic contaminant whose presence is undesirable and potentially harmful to individuals and/or the environment. Examples of contaminated water may include, but are not limited to effluents, leachates from landfills or other waste sites, waste water, and contaminated ground water from sites of chemical plants, mining sites or sites where petroleum products are extracted. Examples of contaminated soils may include, but are not limited to soils contaminated with industrial compounds from sites of production of such compounds, soils at locations of industrial accidents or spills, and the like.

As used herein, the term "rhizome" refers to a mass of roots. The overall root structure includes primary, secondary and tertiary roots. One characteristic of rhizomes is that they can grow horizontally.

As used herein, the term "rhizosphere" refers to a rhizome and its surrounding soil environment. In some circumstances described herein, rhizospheres are contained within a reed bed used to break down contaminants. In context of the methods and systems described herein, a rhizosphere is expected to at least include microorganisms originally present in the soil environment and microorganisms originally present in the rhizome. Furthermore, the rhizosphere may also include microorganisms originally present in a specific sample of contaminated water or a specific sample of contaminated soil which is to be treated by the processes and systems described herein. In this context, a rhizosphere is in a suitable condition for metabolizing contaminants when microorganisms originally present in or on the rhizome, microorganisms originally present in the reed bed soil, and microorganisms originally present in the contaminated water or soil are adapted to each other's presence and providing continuously high biological activity towards metabolizing contaminants. This adaptation may include symbiotic relationships among groups of microorganisms.

As used herein, the term "wetland plant" refers to plants that naturally grow in water within wetlands, which are areas where water covers the soil or is present either at or near the surface of the soil. Typical wetlands consist of marshes or swamps.

As used herein, the term "reed" refers to a slender-leaved plant of the grass family which grows in a wetland or in water. As such, reeds are considered to be wetland plants.

As used herein, the term "effluent" refers to a discharge of industrial waste, sewage or other pollutant which contains contaminants.

As used herein, the term "leachate" refers to water which has percolate through a solid and leached some of the constituents of the solid. Leachates from landfills or industrial sites can contain harmful contaminants.

As used herein, the term "speciation" refers to formation of new and distinct species in the course of evolution. The term is used in context of rapid evolution of microorganisms which occurs on a relatively fast time scale, such as during the course of preparation of soil conditioner.

As used herein, the term "constructed wetland" refers to a type of reed bed technology based on reeds planted in gravel substrates. This is distinct from and not to be confused with a "soil-based rhizosphere flow-through system."

As used herein, the term "soil-based flow-through rhizosphere system" refers to an installation configured to allow water to flow therethrough with the water contacting a soil substrate containing a rhizome as it flows through the system.

As used herein, the term "plate count" refers to a fundamental technique for determining the number of viable microorganism cells in a sample. The sample is spread on an agar plate and incubated to promote growth of the microorganisms on the plate. Colonies of microorganisms are counted with the extent of dilution of the original sample being taken into account. The amounts of microorganisms are typically expressed in units of counts per mL.

As used herein, the term "organic contaminants" refers to any organic compounds whose presence is generally considered undesirable and/or potentially harmful or toxic.

As used herein, the terms "breaking down contaminants," and "metabolizing contaminants" are synonymous and refer to destruction of contaminants via metabolic pathways (breakdown pathways) of microorganisms.

As used herein, the term "thermal desorption" refers to is an environmental remediation technology that utilizes heat to increase the volatility of contaminants such that they can be removed (separated) from the solid matrix.

Description of a General Process Embodiment and Related Equipment

The components and process steps general embodiment will now be described. A number of possible alternative features are introduced during the course of this description. It is to be understood that, according to the knowledge and judgment of persons skilled in the art, such alternative features may be substituted in various combinations to arrive at different embodiments of the present invention.

An illustration of one embodiment of a process including the main steps involved in construction of a large-scale soil-based flow-through rhizosphere system is shown in FIG. 1. It is shown that a test bioreactor is prepared with a soil-based rhizosphere system and configured for inflow of contaminated water and outflow of flow-through water which may or may not have had a significant degree of decontamination at the outset. Flow of contaminated water through the test bioreactor is maintained until it is found that an equilibrium state has been attained (as determined by collection of data) wherein the microbial population has been stabilized by the conditions. The microbial population will include microorganisms originally present in the contaminated water and originally present in the rhizome of the plant and the soil within the test bioreactor. With attainment of equilibrium deemed to be sufficient for further development of a larger-scale system, a sample of the rhizosphere is obtained from the bioreactor and homogenized. A microbial suspension is extracted from the homogenized mixture. This microbial suspension is reasonably assumed to include at least some of the microorganisms originally present in the contaminated water and at least some of the microorganisms originally present on and within the rhizome as well as the soil in the test bioreactor. The microbial suspension is incubated and fed nutrients to promote growth of the microorganisms to increase the concentration of total microorganisms, thereby providing the soil conditioner. The soil conditioner is applied to the soil within a large-scale contained area to increase the soil content of microorganisms that can metabolize contaminants. Then the same plant used in the test bioreactor is installed in greater numbers in the soil of the large scale contained area in the final step of construction of the large-scale soil-based flow-through rhizosphere system.

Additional detail regarding various aspects, process steps and components of this general embodiment will now be described under separate headings.

Wetland Reeds and Plants

The term "reed" is a common name used to identify several tall grass-like plants which grow in wetlands. A preferred reed for use in embodiments of the process and system of the invention is *Phragmites australis* due to this wetland species being generally regarded as having the greatest root mass and production of oxygen. These are favorable characteristics for embodiments of the process of the invention. Any other wetland reed species or non-reed species that have a root mass that provides oxygen into the ground will exhibit a similar activity although possibly at lower levels. As such, other wetland plant species may be employed in embodiments of the process of the present invention. Examples of other reed species include, but are not limited to *Arundo donax* L., *Neyraudia reynaudiana*, *Phalaris arundinacea*, *Glyceria maxima*, *Elegia tectorum*, *Thamnochortus insignis*, species of the genus *Calamagrostis*, species of the genus *Sparganium*, and species of the genus *Typha*. The selection of the wetland plant for use in various embodiments of the process and system of the invention will depend on a number of factors such as soil compatibility, climate at the location of installation, and the characteristics of the selected plant itself, for example. Plants other than reeds may be found to have favorable characteristics and, as such, may be adaptable for use in various alternative embodiments of the invention.

Reed Tub Test Bioreactor

A container with a volume ranging from about 10 L to about 50 L, preferably about 25 L in volume with an inlet and outlet which allows for the flow and control of input of contaminated water, is filled with a soil matrix which may be composed of topsoil or another class of soil. Other components may be added as deemed required to aid in growth of the plant and its rhizome or to increase flow of water through the container. Such components may include various organic additives as well as sand to provide additional water permeability. This mixture is planted with rhizome plant material such as *Phragmites australis* and the plants are allowed to develop and grow to the point that the container becomes a rhizosphere full of rhizome plant material.

In addition to a liquid conduit arrangement that allows liquids to flow through the container (by passage through the soil/plant matrix), valves are included to retain liquids within the container without flow in situations where halting the flow through the container is desired.

General Identification of Microorganisms Present in Contaminated Water or Contaminated Soil It is advantageous to analyze a sample of the contaminated water or contaminated soil which is to be treated using the soil-based flow-through rhizosphere system. To do this, any microbiological identification method or process may be used, from culture on agar plates to genetic-based analyses. Generally, growth of microorganisms on plates in a manner which permits their identification may be a useful process step. However, identification of the microorganisms at the species and strain level, while potentially advantageous, is not necessary. Microorganisms in contaminated water such as effluents and leachates are known to include bacteria, algae and fungi. Although not all three classes are always present, bacteria are usually present in contaminated water or contaminated soil and usually through natural selection processes, have the ability to metabolize the organic contaminants therein. Generally, the quantity of bacteria present in the contaminated water or contaminated soil is an indicator of the likelihood that certain species and strains of bacteria in the contaminated water or contaminated soil will adapt under the bioreactor conditions to metabolize the contaminating compounds. In situations where the quantity of bacteria in the contaminated water or contaminated soil is deemed to be very low, the contaminated water or contaminated soil is inoculated with a publically-available mixture of bacteria which would be expected to contain bacteria that could adapt and speciate appropriately to metabolize the contaminants. Such bacterial mixtures can be identified by a person having ordinary skill in the art, without undue experimentation.

Introduction of Contaminated Water into a Reed Tub Test Bioreactor

The contaminated water is introduced into the test bioreactor via one or more inlet conduits and the rate of flow of water into and out of the box is measured. It is helpful to determine the maximum volume which can pass through the system over a given period of time without flooding the test bioreactor.

Indicators of the system such as pH, dissolved oxygen and electrical conductivity are measured together with the oxidation-reduction potential of the system, which is an indicator of aerobic/anaerobic state of the below surface condition of the soil rhizosphere solution.

After a period of time, once steady state conditions have been achieved, as evidenced by the data indicators, the microbial population is assessed. This is typically done with a basic plate count using standard plates and nutrients. Additionally, some indicator of a concentration of a microbial species of interest will be added to the analytical parameters. This for example may be the simple chemical oxygen demand (COD) as a measure of declining contaminant concentration, or UV, GC or mass spectrometry analysis, depending on the nature of the species of interest.

In some situations where contaminant compounds are particularly complex and difficult to metabolize, a co-metabolite such as a carbohydrate may be added to increase metabolic activity of the microbial species present.

Organic compounds are known to break down through specific metabolic pathways which produce metabolite compounds. It is therefore possible to determine the concentration of a particular metabolite at the inlet and outlet of the container and also to search for the metabolites generated within the system. This allows the possibility that the compound is simply being removed from solution by simple soil adsorption and the compound as well as its metabolites can be tracked through the system by the methods outlined above.

The process of degradation and breakdown may take anywhere between 1 to 8 weeks before soil organisms can respond to give complete degradation of the target compound. In this period the small quantities of incipient bacteria usually of about $10^2$ counts/mL or less, will have risen to about $10^6$ to $10^9$ counts/mL. During this process, and depending on the concentration of the material to be degraded, the system may have shifted to an anaerobic condition and/or an altered pH condition. These conditions are intermittently or continuously monitored to avoid potential problems arising from dynamic conditions that can affect the rate of metabolic breakdown of the contaminants.

If the trial is successful and clear evidence exists for degradation of the target compound, then the next stage of the operation can be carried out. Otherwise, the process steps outlined hereinabove are repeated under different conditions.

Extraction and Concentration of Microorganisms to Produce Soil Conditioner

The next step in the operation is to extract and increase the soil rhizosphere with microorganisms whose symbiotic relationship have produced the degradation. These total microorganisms include microorganisms originally present in the contaminated water and present on and within the rhizome of the wetland plant, as well as microorganisms present in the soil containing the rhizome of the wetland plant. A portion of rhizome and rhizosphere soil is homogenized and placed into a container in the presence of a nutrient mixture, such as a sugar/molasses mixture for example, with the temperature maintained at about 30° C. for a period of about 7 to about 10 days, producing a concentrated liquid containing the appropriate microorganisms. This concentrated liquid is hereinafter referred to as the "soil conditioner." While not typically characterized to determine relative amounts of specific microorganisms in the soil conditioner, it is believed that the soil conditioner includes a population of microorganisms which will function symbiotically or otherwise cooperatively in metabolic breakdown of the contaminants of the contaminated water or contaminated soil.

Application of the Soil Conditioner to the Soil of the Flow-Through Rhizosphere System or Contaminated Soil at a Contaminated Site The soil conditioner is diluted and sprayed onto the soil growing matrix which is to be used within the full-scale flow-through rhizosphere system. The wetland plant is then planted in this soil matrix. Alternatively, the soil conditioner may be added to a wide area of contaminated soil at a contaminated site without planting a wetland plant. The microorganisms carefully developed and speciated during preparation of the soil conditioner are introduced as significant populations into the full-scale flow-through rhizosphere system. Therefore, the application of the soil conditioner that has been produced specifically for the specific contaminated water being treated provides the following: (i) a reduction of the required establishment period, thereby reducing the time required to bring the system on-line after construction, (ii) a reduction of risk required to be imposed on the client, by the technology provider, (iii) an increase in confidence that the treatment system will perform as designed, therefore limiting risk of non-performance penalties being triggered and/or allowing increased value of guarantees to be provided to the client, (iv) a reduced requirement for pilot treatment systems where pilot systems are deemed necessary by the technology provider, and (v) an increased market due to increased treatment capabilities and therefore less restriction on the complexity of the chemical compounds that can be treated.

Flow Conduits in the Flow-Through Rhizosphere System

Prior to planting the wetland plant in the flow-through rhizosphere system, the soil treated with the soil conditioner is provided with at least one conduit for flowing the contaminated water into the rhizosphere system and at least one conduit outlet to allow discharge of de-contaminated water from the system. The arrangement of conduits may be provided in essentially any configuration which allows the contaminated water to disperse across as much of the rhizosphere in the system as possible. It is believed that the large surface area of soil particles allows more efficient penetration of water to occur across the entire soil bed to allow the microorganisms to metabolize the contaminants.

Some embodiments employ a system constructed for a predominantly horizontal flow of water dispersed across the rhizosphere wherein the input of contaminated water will flow to one or more exit points not varying appreciably in elevation relative to the input elevation, while other embodiments employ a system constructed for a predominantly vertical flow of water wherein the input of contaminated water will flow to one or more exit points which are significantly lower in elevation relative to the input elevation. It is to be understood that diffusion of oxygen occurs more readily within shallower soil installations than in deeper soil installations. As a result, microorganisms with anaerobic metabolic pathways being used in the breakdown of contaminants will be expected to operate more effectively in vertical flow arrangements with deeper soil beds and microorganisms with aerobic metabolic pathways will be expected to operate more effectively in horizontal flow arrangements. In some embodiments, a complete treatment system may include both horizontal flow and vertical flow arrangements operating sequentially, as described in Example 1. The sequence may be determined through testing using small scale treatment systems.

Establishment of Microorganisms in the Flow-Through Rhizosphere System

Without necessarily being bound to any particular theory, it is believed that, within natural attenuation, a small quantity of bacteria, either anaerobic or supported by small scale diffusion of atmospheric oxygen, is responsible for initiating breakdown of contaminants in water. The processes described herein include preparation of a test bioreactor container which includes the wetland plant rhizosphere soil matrix with an initially-expected level of bacteria of $10^2$ counts/mL or less. The contaminated water is then flowed through the test bioreactor to provide an equilibrium condition wherein the bacteria are in consistent contact with the contaminants. Equilibrium may be evidenced by confirmation that some level of breakdown of the contaminants is occurring. An extract of soil and rhizome representing the rhizosphere is obtained from the test bioreactor. This extract is expected to contain microorganisms which were originally present in the contaminated water as well as microorganisms originally present in the soil and on and within the rhizome of the wetland plant. This extract is subjected to conditions to increase the levels of the microorganisms, such as incubation and addition of nutrients. For example, the level of bacteria may be increased from $10^2$ counts/mL to as much as $10^9$ counts/mL). This extract is referred to herein as "soil conditioner." The soil conditioner is then used to treat the soil bed of a large scale rhizosphere flow through system prior to planting of the wetland plant into the soil bed. This ensures that the soil contains the microorganisms at sufficient levels to provide relatively high levels of metabolism of the contaminants during flow through of the contaminated water to generate a relatively high rate of degradation of the contaminants.

The soil matrix provides soil support and mineral nutrients for the plant and support material for the soil bacteria and other soil organisms to populate. The wetland plants provide a stable secondary rooted structure within the soil that allows for a high rate of passage of the water containing the contaminant through the system. The wetland plants provide an oxygen supply to the aerobic bacteria and soil organisms, whilst the anaerobic organisms are located in areas of the soil bed away from the oxygenating root system. Consequently, any contaminant moving through the system will experience oxidative and reductive situations as they move through the system's wetland plants. One preferred wetland plant used in various embodiments of the invention is *Phragmites australis*. This plant is generally regarded as providing the greatest root mass and oxygen input.

Alternative Uses of the Soil Conditioner

Various embodiments of the soil conditioner, prepared under various conditions with exposure to various contaminants, will be applicable for treatment of contaminated water with various organic contaminants including industrial effluents, leachates from landfills and industrial sites, groundwater, tailings ponds and produced water from oilfields.

Various embodiments of the soil conditioner are expected to be applicable for ex-situ soil remediation. In this instance, contaminated soils would be used within the initial soil growing matrix and the breakdown process described previously for contaminated wastewaters would similarly breakdown organic contaminants found within contaminated soil.

Various embodiments of the soil conditioner could also be applied in the field of in-situ soil remediation, in a way that would be more resilient and robust than current soil remediation methods. Current soil remediation methods generally extract a single species of microorganism, concentrate it and spray back onto the contaminated soil/land. However, certain embodiments of the soil conditioner have concentrated microorganisms with a more diverse population of species that when applied would potentially surpass the treatment potential of current methods as well as reducing the requirement for reapplication of the microorganisms onto the contaminated soil or land.

EXAMPLES

Embodiments of the invention will now be described with reference to the following example below, which is intended to be illustrative and not limiting.

Example 1: Treatment of Chlorosolvent Contaminated Groundwater at an Industrial Site The applicant was requested by a national petroleum company to investigate the feasibility of using soil based reed beds for the treatment of contaminated groundwater within a petrochemical complex. A vinyl chloride production plant was undergoing decommissioning and environmental surveys of the site had shown the presence of 1,2-dichloroethylene and vinyl chloride within the groundwater. As such, the petroleum company required a passive treatment system to remediate the groundwater to acceptable contaminant levels.

Prior to undertaking engineering design work, preparatory investigations were undertaken to assess site conditions and enable concept design calculations to be made. Groundwater contaminant data available from 26 borehole clusters (each cluster containing shallow and deep boreholes) was used to model contaminant plumes for 1,2-dichloroethylene and vinyl chloride. Trial pits were excavated to assess the underlying strata and soil types. Percolation tests were carried out to assess feasibility for soak-away based passive discharge. A topographical survey was undertaken to provide site levels. A microbial assessment of the groundwater was carried out.

This initial research indicated that the surface "soils" included permeable unconsolidated sand, consistent with the majority of the surrounding coastal area. Whilst being extremely suited to a soak-away based discharge, the sand material would have a negative effect on the successful implementation of a soil based reed bed treatment system, due to the low particle surface area to volume ratio of the sand based soils.

Additionally, sand based soils are inert and therefore have a low presence of natural bacteria in comparison to the loamy topsoils used within standard soil based reed bed technology. The consequence of installing a reed bed treatment system with a low startup microbial population is a lengthy establishment phase whilst bacterial populations multiply to the required levels for treatment to occur within the designed residence time. In order to counter the problems associated with the site soils, an alternative methodology to the standard implementation of soil based reed bed technology was devised and used.

It was determined that low levels of bacteria existed within the groundwater contaminant plume, indicating that contaminant breakdown may be occurring at minor quantities within the plume environment. Chemical analysis confirmed the presence of contaminant breakdown products, providing further indication that a very low level of remediation by bacteria in the groundwater was taking place.

However, the pedology of the site was found to be dominated by permeable unconsolidated sand. There were very few sites available therefore for the bacteria to associate with clay or organic matter which would enable them to stabilize and flourish. In essence therefore, the rates of natural attenuation/remediation were extremely low.

In order to harness the metabolic power of the microorganisms already present, it was deemed necessary to increase the population density of these microorganisms.

The first step was to expose the reed plants that were to be used, in a controlled manner to the contaminated groundwater in a test bioreactor. This was undertaken within several duplicated small test systems. This was necessary to: i) establish that the contaminated groundwater was not toxic to the strain of reed used; ii) introduce the bacterial types present in the contaminated groundwater to the plant rhizosphere; iii) establish a rhizosphere system where the plant root and bacteria are working symbiotically to produce co-metabolites; and iv) ensure that the bacterial populations produced could be established and fixed within the designed soil matrix, rather than being transported out under hydraulic flow.

In situations where the concentrations of contaminants are high and complex in mixture, the rates of degradation under natural attenuation will usually be unacceptably low, and timescales far too long for genuine remediation to take place without some degree of enhancement. This was particularly relevant for this particular site, where the composition of the soil was unsuitable for sustaining high microbial counts.

Therefore a soil mixture was designed to be comprised of the following components: i) pre-existing site materials, sandy in nature, with the inorganic components screened to provide a consistent low particle size, ii) clay content with a high cation exchange equivalent, in this case bentonite, and iii) organic matter containing humic and fungal material.

The above components were mixed in varying proportions to create the matrix to be used in the test systems. The test systems were comprised of 20 L high-density polyethylene boxes, filled with the matrix soil and planted with the selected reed. Outlet piping comprised a simple level control so as to retain water within each individual test system. The test systems were filled with varying strengths and dilutions of contaminated groundwater. The water level within the test systems was maintained 20 mm below soil level throughout the duration of the procedure. The test systems were monitored with conventional water quality instrumentation such as pH, oxidation-reduction potential (ORP), and chemical oxygen demand (COD). Microbial counts were periodically taken for the different systems to ensure appropriate development of microbial populations.

After a period of 8 weeks all botanical, biological, chemical and microbial indicators were positive, indicating an appropriate point for transition to the next stage.

Having carried out the trials and successfully created a soil rhizosphere rich in bacteria, a portion of the soil rhizosphere matrix was extracted and homogenized. The homogenizing reduces plant material inside and outside the rhizome wall to fine particle size and also releases sugars from the rhizsosphere into solution. The solution was then boosted with nutrients and fermented in a closed glass vessel at a temperature of approximately 30° C. for a minimum period of 5 days. The microorganism count after this period had increased dramatically and the solution was considered ready for use as a soil conditioner. The stability of the soil material remains constant for approximately 1 month, if stored out of direct sunlight and below 20° C.

A dilution of 100:1 of the soil conditioner was prepared with deionized water and applied to a series of temporary lagoons which housed potted reed stock of *Phragmites australis*, within an on-site nursery. The contaminated water was flowed through the arrangement of pots containing the plants in the lagoon. The temporary lagoons were maintained over a period of 1 month prior to transplantation of the reeds into a soil-based system. It is to be understood that although this step of using temporary lagoons is included in the present example, it may not be required in all cases.

In addition, a dilution of 100:1 of the soil conditioner was prepared with deionized water and applied via a spray applicator to all soils during the mixing process. This was carried out immediately prior to placement of the soils within the system and prior to planting of the reeds in the soil.

Figure 2:
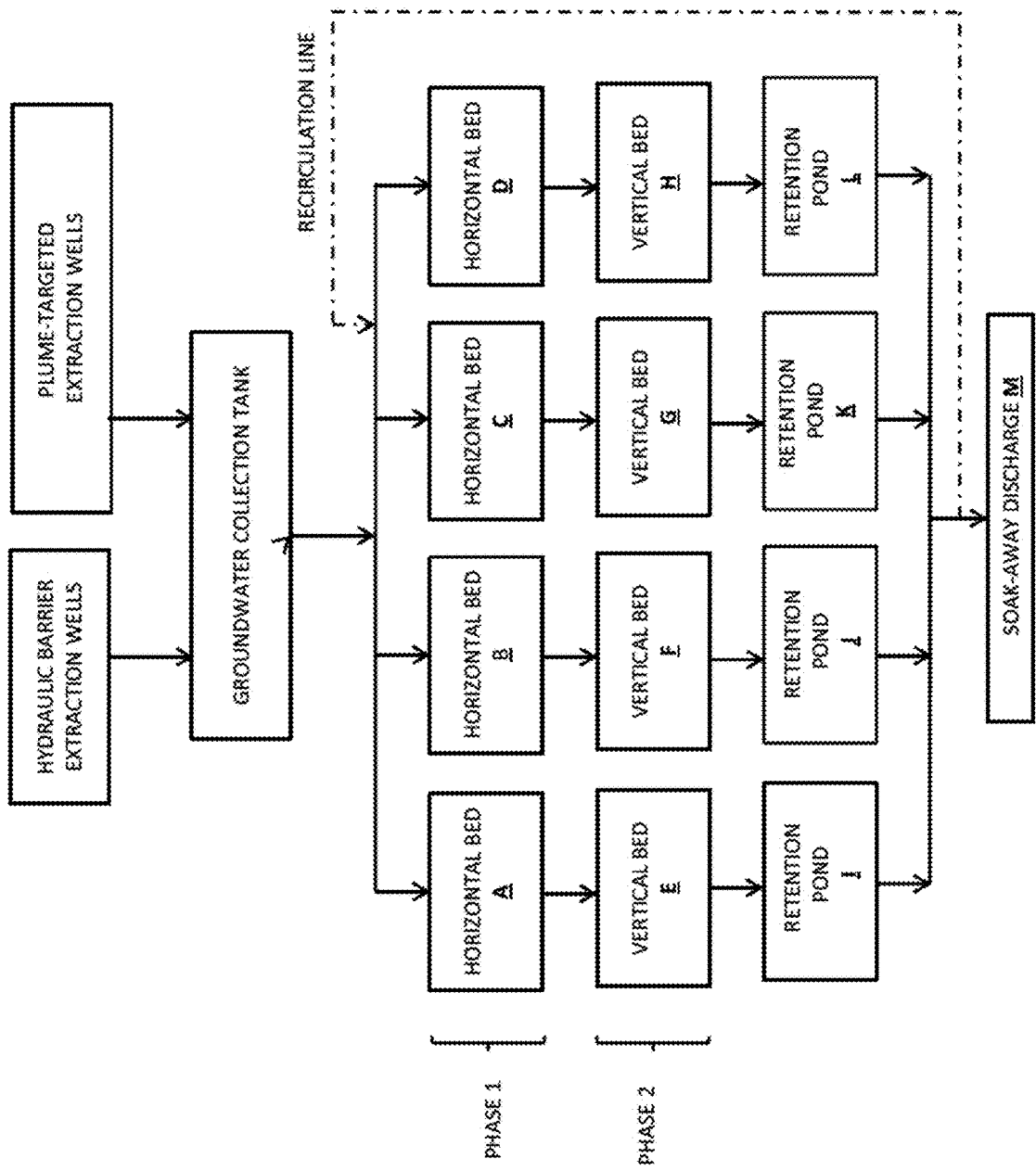
FIG. 2 is a flow chart of an embodiment of a two-phase process for breaking down contaminants in contaminated water using a soil-based rhizosphere flow-through system, according to Example 1.

The flow of contaminated water and configuration of reed beds used in this example is illustrated in FIG. 2. Contaminated groundwater was pumped from extraction wells located at the hydraulic barrier of the industrial site (16 extraction wells producing a total of 160 $m^2$/day) and also pumped from extraction wells located within the known underground plume of contaminants (3 wells producing a total of 140 $m^2$/day).

The extracted contaminated groundwater was then conveyed to a groundwater collection tank. A flow of the contaminated groundwater from the groundwater collection tank was established and split into four inlet conduits for entry into four separate identical reed beds (labelled A to D in FIG. 2), each having a soil depth between about 0.4 m to about 0.5 M. At this depth of soil, the flow of water is generally horizontal from the inlet to the outlet and the metabolism of contaminants by the established microorganisms occurs predominately via aerobic metabolic pathways. This represents Phase 1 of this particular process. In Phase 2, water treated by the horizontal beds A-D is conveyed from outlets in these beds to corresponding vertical beds E-H, each having a soil depth between about 0.8 to about 1.0 m. At this depth of soil, the flow of water is generally vertical from the inlet to the outlet and the metabolism of contaminants by the established microorganisms occurs via a combination of aerobic and anaerobic metabolic pathways, wherein anaerobic metabolism will be more likely to occur at locations near the bottom of the vertical reed beds. This represents Phase 2 of this particular process. It is to be understood that while the present example employs a two-phase treatment process, depending on the class of contaminant and the microorganisms in the rhizosphere, it may be possible to sufficiently decontaminate water using only a single phase treatment process. In other situations, more than two phases may be required. The molecular complexity of any individual contaminant and the types of biochemical reactions required to metabolize it are expected to represent important factors in the resulting complexity of the flow-through rhizosphere system.

After treatment in the Phase 2 vertical reed beds (E-H), in this particular example, the treated water is conveyed to corresponding retention ponds (I-L). The provision of corresponding retention ponds provides a margin of safety in the event that an individual upstream reed bed fails for any reason to decontaminate the contaminated water to a sufficient level. Each retention pond may be tested separately to confirm that sufficient decontamination has occurred before ultimately releasing its treated water into a soak-away discharge container M.

In FIG. 2, a recirculation line is shown extending from the soak-away discharge inlet back to the main inlet to the horizontal beds. Such a recirculation line could also be provided to one of the individual horizontal bed inlets, in order to repeat the treatment steps if desired.

Figure 3:
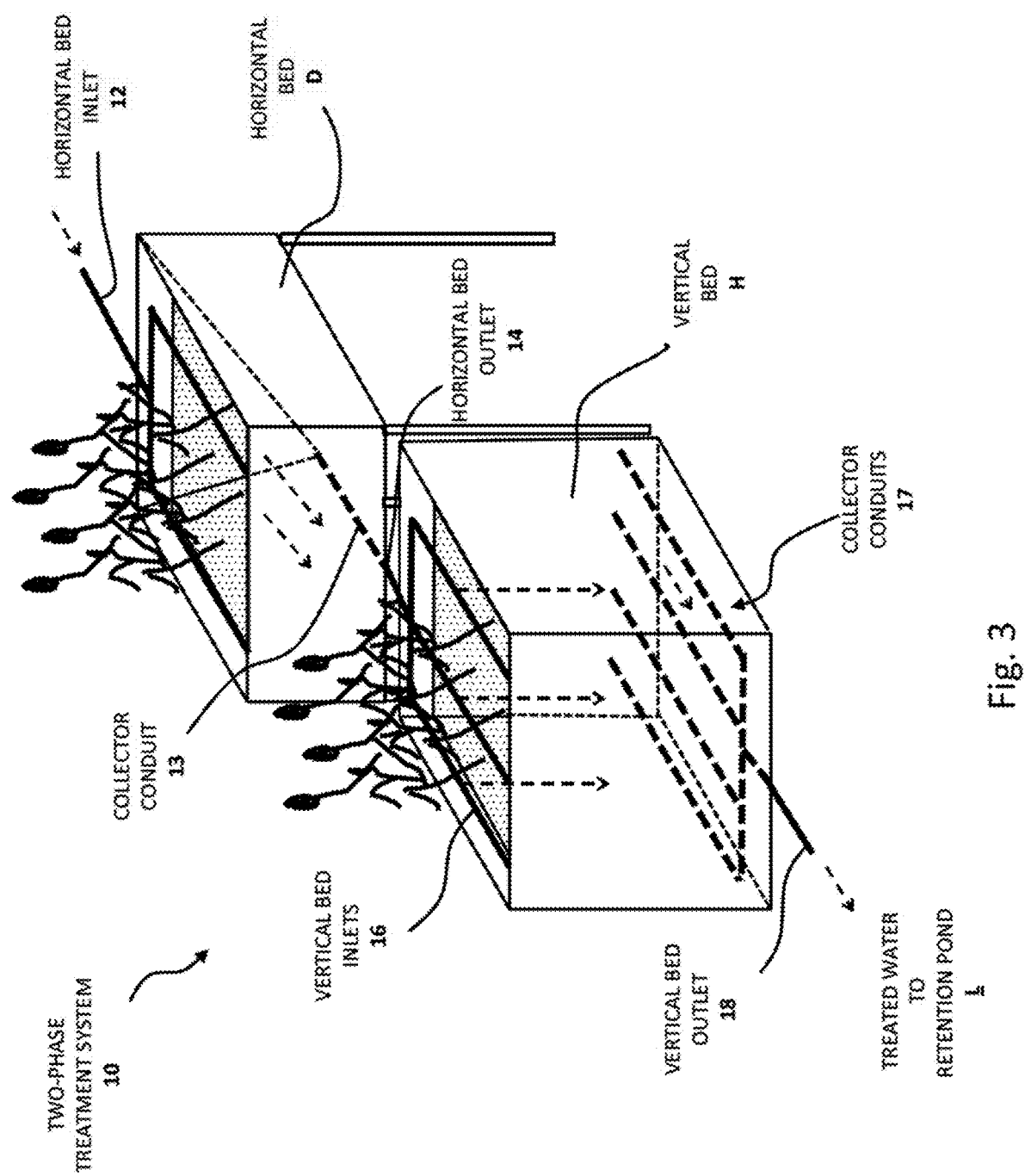
FIG. 3 is a perspective illustration of a two-phase treatment system 10.

FIG. 3 is a perspective illustration of water flow through a two-phase treatment system 10, showing flow of contaminated water to horizontal bed D and subsequently through the corresponding vertical bed H, as would be provided in the flow scheme of FIG. 2. While the presence of plants is shown, their rhizomes are omitted in an attempt to preserve clarity but should be understood to be present. Horizontal inlet 12 bifurcates into two arms above the soil level in horizontal bed D and disperses contaminated water onto the surface of the soil where it then moves generally horizontally across the bed D. The contaminants are subjected to metabolism by primarily aerobic metabolic pathways and the water collects in a collector conduit 13 and flows to the horizontal bed outlet 14. The horizontal bed outlet 14 joins the vertical bed inlet 16 which is split into three arms to disperse the partially treated water onto the soil of the vertical bed H (which is about twice the depth of the horizontal bed D). The water percolates downward within the soil bed with remaining contaminants and/or metabolites thereof are further processed by aerobic and anaerobic metabolic pathways. Near the bottom of vertical bed enters a series of four collector conduits 17, which extend to the vertical bed outlet 18. The treated water is then sent to retention pond L.

Figure 4:
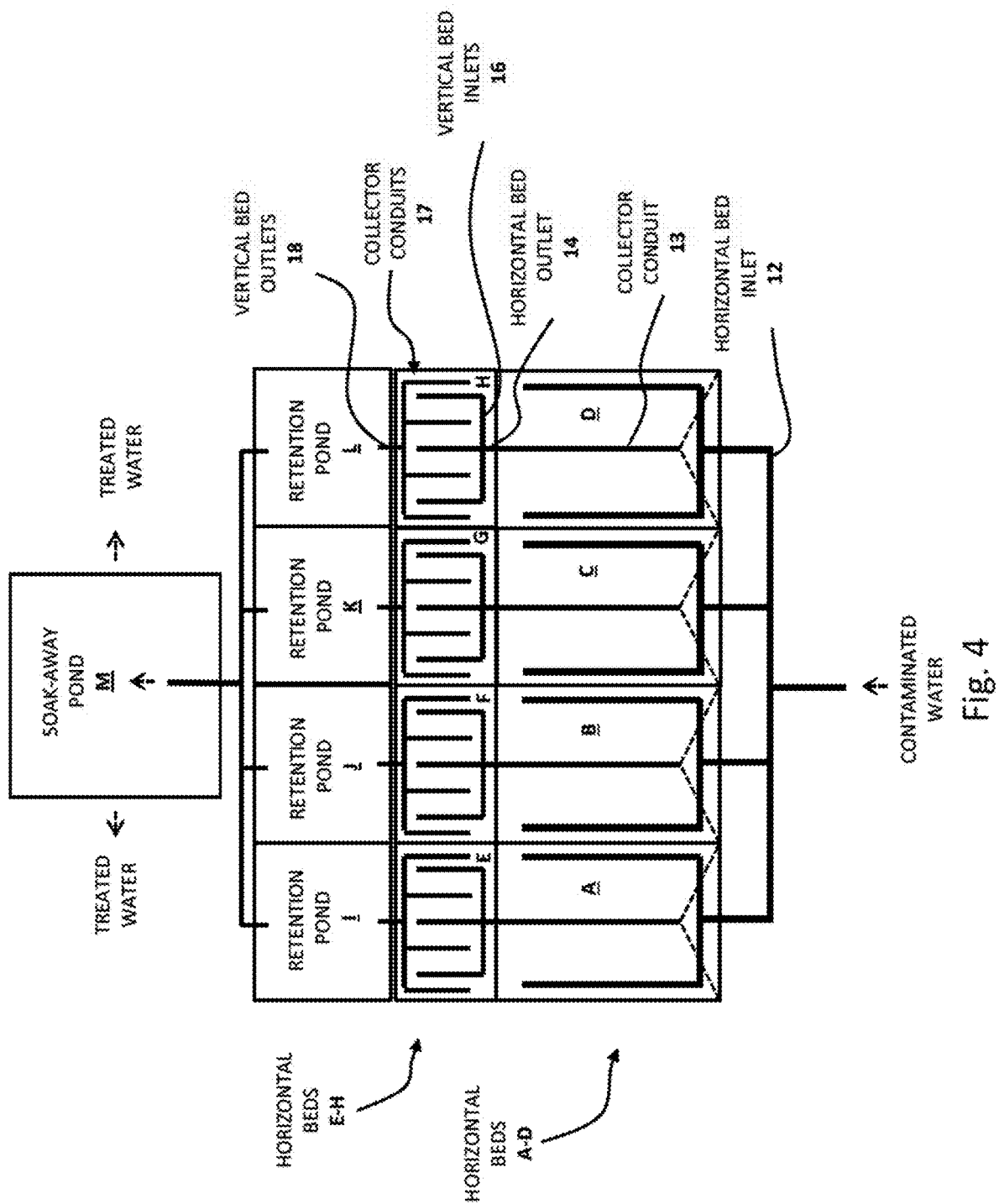
FIG. 4 is a plan view showing a soil-based rhizosphere flow through system with an arrangement of horizontal beds (A-D) for a first phase, an arrangement of corresponding vertical beds (E-H) in a second phase, and a series of corresponding retention ponds (I-L) as well as inlets, outlets and collector conduits used in the system.

FIG. 4 illustrates a plan view of the large scale modular system used to treat the contaminated groundwater. The system includes a battery of reed beds including four horizontal beds A-D, four corresponding vertical beds E-H, four corresponding retention ponds I-L and a single soak away pond M. Also shown are the main horizontal bed inlet 12, collector conduit 13, horizontal bed outlet 14, vertical bed inlets 16, collector conduits 17 and vertical bed outlet 18 which extends to retention pond M. Labelling of inlets, outlets and conduits in the remaining six beds is omitted in an effort to preserve clarity. It is to be understood however, that in this particular example, all horizontal beds are substantially identical to each other with similar inlets, outlets and conduits and all vertical beds are likewise substantially identical to each other with similar inlets, outlets and conduits.

Upon introduction of the feed of contaminated water into the large-scale soil-based flow-through rhizosphere system, monitoring of concentration levels (mg/L) of 1,2-dichloroethylene was conducted at the point of system feed (prior to treatment), the phase 1 outlet (treatment with horizontal beds only) and final discharge (sequential treatment with horizontal and vertical beds). The raw data are listed in Table 1 below with average concentrations of 1,2-dichloroethylene presented on the last line of the table. The data are also presented as linear plots in FIGS. 5-7.

TABLE 1

Raw Data - Concentrations of 1,2-Dichloroethylene

| Date | System Feed (mg/L) | Phase 1 Outlet (mg/L) | Final Discharge (mg/L) |
|---|---|---|---|
| 18 Jul. 2016 | 118.38 | 36.83 | 6.3 |
| 19 Jul. 2016 | 108.12 | 36.05 | 4.96 |

TABLE 1-continued

Raw Data - Concentrations of 1,2-Dichloroethylene

| Date | System Feed (mg/L) | Phase 1 Outlet (mg/L) | Final Discharge (mg/L) |
|---|---|---|---|
| 20 Jul. 2016 | 109.87 | 23.12 | 1.37 |
| 21 Jul. 2016 | 115.57 | 21.14 | 1.16 |
| 22 Jul. 2016 | 102.26 | 18.15 | 3.78 |
| 23 Jul. 2016 | 112.52 | 16.39 | 2.62 |
| 24 Jul. 2016 | 103.54 | 14.56 | 5.69 |
| 25 Jul. 2016 | 131.09 | 9.82 | 2.13 |
| 26 Jul. 2016 | 99.15 | 11.6 | 2.55 |
| 27 Jul. 2016 | 97.74 | 16.5 | 2.11 |
| 28 Jul. 2016 | 143.01 | 11.95 | 0.59 |
| 29 Jul. 2016 | 118.46 | 13.77 | 0.51 |
| 30 Jul. 2016 | 110.6 | 11.99 | 2.18 |
| 31 Jul. 2016 | 121.78 | 12.56 | 1.8 |
| 1 Aug. 2016 | 139.21 | 4.4 | 0.45 |
| 2 Aug. 2016 | 100.82 | 13.32 | 0.18 |
| 3 Aug. 2016 | 109.94 | 9.93 | 0.45 |
| 4 Aug. 2016 | 104.65 | 12.05 | 0.18 |
| 5 Aug. 2016 | 110.96 | 2.74 | 0.9 |
| 6 Aug. 2016 | 117.08 | 5.34 | 0.67 |
| 7 Aug. 2016 | 113.35 | 7.73 | 5.02 |
| 8 Aug. 2016 | 136.01 | 8.89 | 1.84 |
| 9 Aug. 2016 | 104.84 | 9.82 | 6.29 |
| 10 Aug. 2016 | 122.85 | 5.27 | 0.62 |
| 11 Aug. 2016 | 125.76 | 5.65 | 3.52 |
| 12 Aug. 2016 | 140.05 | 12.52 | 0.1 |
| 14 Aug. 2016 | 112.52 | 7.55 | 1.42 |
| 15 Aug. 2016 | 115.58 | 11.76 | 1.52 |
| 16 Aug. 2016 | 127.37 | 9.85 | 1.76 |
| 17 Aug. 2016 | 102.47 | 8.04 | 1.24 |
| 18 Aug. 2016 | 107.42 | 14.36 | 1.01 |
| 19 Aug. 2016 | 103.69 | 13.28 | 0.75 |
| 20 Aug. 2016 | 98.72 | 9.42 | 3.83 |
| 21 Aug. 2016 | 118.25 | 8.77 | 3.53 |
| 22 Aug. 2016 | 148.89 | 8.92 | 4.44 |
| 23 Aug. 2016 | 122.86 | 7.07 | 0.62 |
| 24 Aug. 2016 | 94.61 | 4.73 | 0.23 |
| 25 Aug. 2016 | 92.66 | 12.7 | 3.41 |
| 26 Aug. 2016 | 123.82 | 10.31 | 4.03 |
| 27 Aug. 2016 | 128.83 | 7.96 | 1.03 |
| 28 Aug. 2016 | 152.52 | 12.73 | 6.47 |
| 29 Aug. 2016 | 142.35 | 16.37 | 4.84 |
| 30 Aug. 2016 | 138.2 | 17.27 | 4.23 |
| 31 Aug. 2016 | 153.63 | 3.88 | 0.83 |
| 1 Sep. 2016 | 128.91 | 2.15 | 0.48 |
| 2 Sep. 2016 | 117.17 | 13.24 | 0.68 |
| 3 Sep. 2016 | 173.69 | 14.58 | 0.53 |
| 4 Sep. 2016 | 147.54 | 14.02 | 2.8 |
| 5 Sep. 2016 | 129.79 | 12.57 | 2.71 |
| 6 Sep. 2016 | 123.52 | 11.55 | 2.46 |
| 7 Sep. 2016 | 125.37 | 10.79 | 1.7 |
| 8 Sep. 2016 | 125.84 | 7.04 | 0.01 |
| 9 Sep. 2016 | 123.53 | 6.63 | 0.01 |
| 10 Sep. 2016 | 123.43 | 6.48 | 0.01 |
| 11 Sep. 2016 | 155.27 | 18.81 | 4.96 |
| 12 Sep. 2016 | 150.1 | 19.48 | 2.28 |
| 13 Sep. 2016 | 148.68 | 6.87 | 8.76 |
| 14 Sep. 2016 | 119.27 | 15.3 | 5.15 |
| 15 Sep. 2016 | 134.35 | 10.81 | 2.78 |
| 16 Sep. 2016 | 138.95 | 15.18 | 4.83 |
| 17 Sep. 2016 | 172.23 | 14.76 | 1.39 |
| 18 Sep. 2016 | 127.89 | 6.99 | 0.35 |
| 19 Sep. 2016 | 100.7 | 12.27 | 0.33 |
| 20 Sep. 2016 | 115.73 | 2.49 | 0.01 |
| 21 Sep. 2016 | 116.22 | 3.19 | 0.14 |
| 23 Sep. 2016 | 109.82 | 3.41 | 0.68 |
| 24 Sep. 2016 | 159.42 | 12.23 | 5.72 |
| Avg. Conc. | 124.2 | 11.58 | 2.25 |

The results indicate immediate and substantial reductions of 1,2-dichloroethylene by the system. Throughout the course of the performance test, treatment phase 1 provided an average contaminant reduction of 93.5%. When combined with treatment phase 2, the average contaminant reduction increased to 98.7%.

Figure 5:
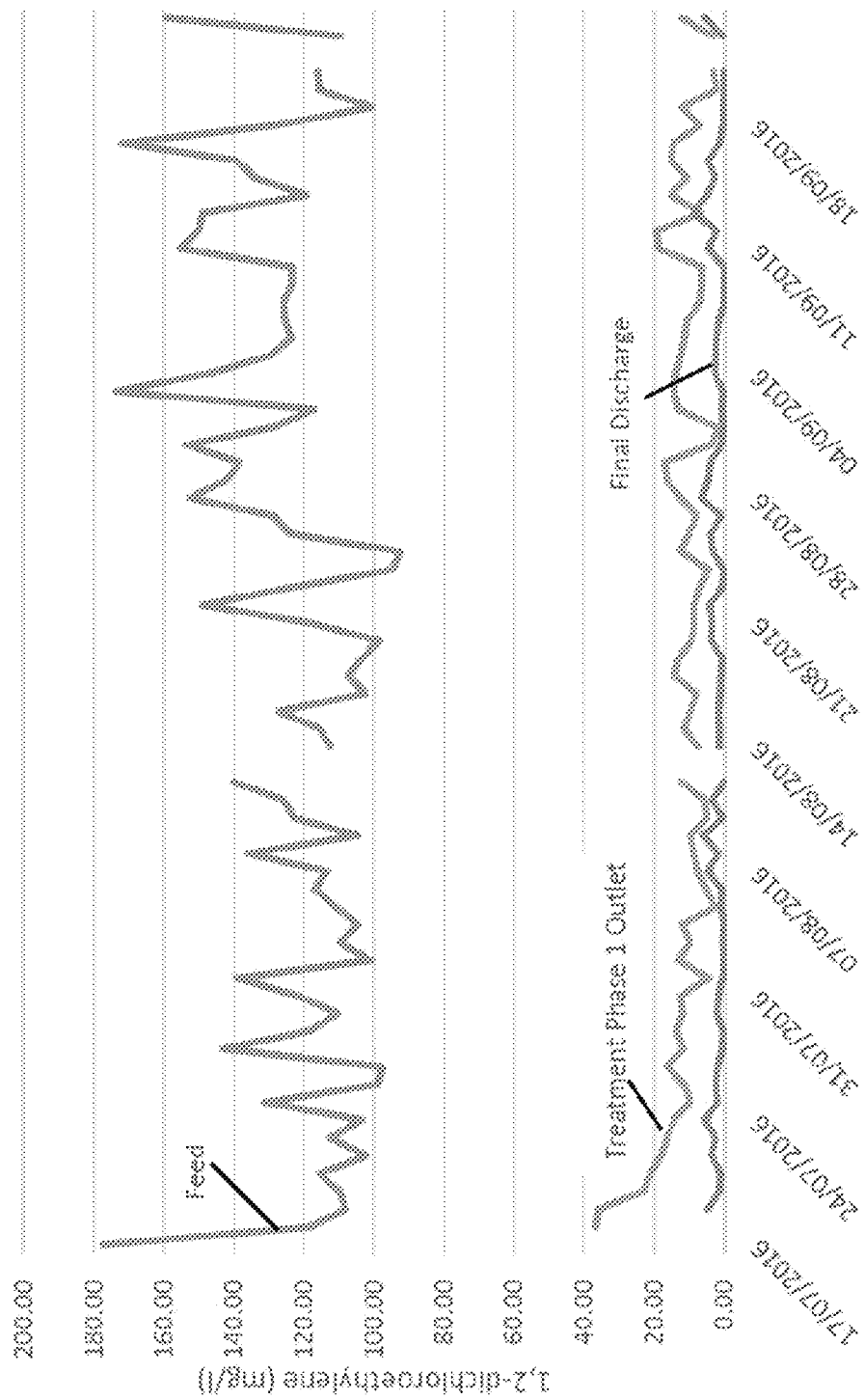
FIG. 5 is a plot of concentrations of 1,2-dichloroethylene vs. time with daily measurements at three different points in the system of FIG. 4, providing evidence of effective breakdown of contaminants.

FIG. 5 shows linear plots comparing the sample analysis results measured at the untreated groundwater feed, the phase 1 treatment outlet and the final discharge outlet.

Figure 6:
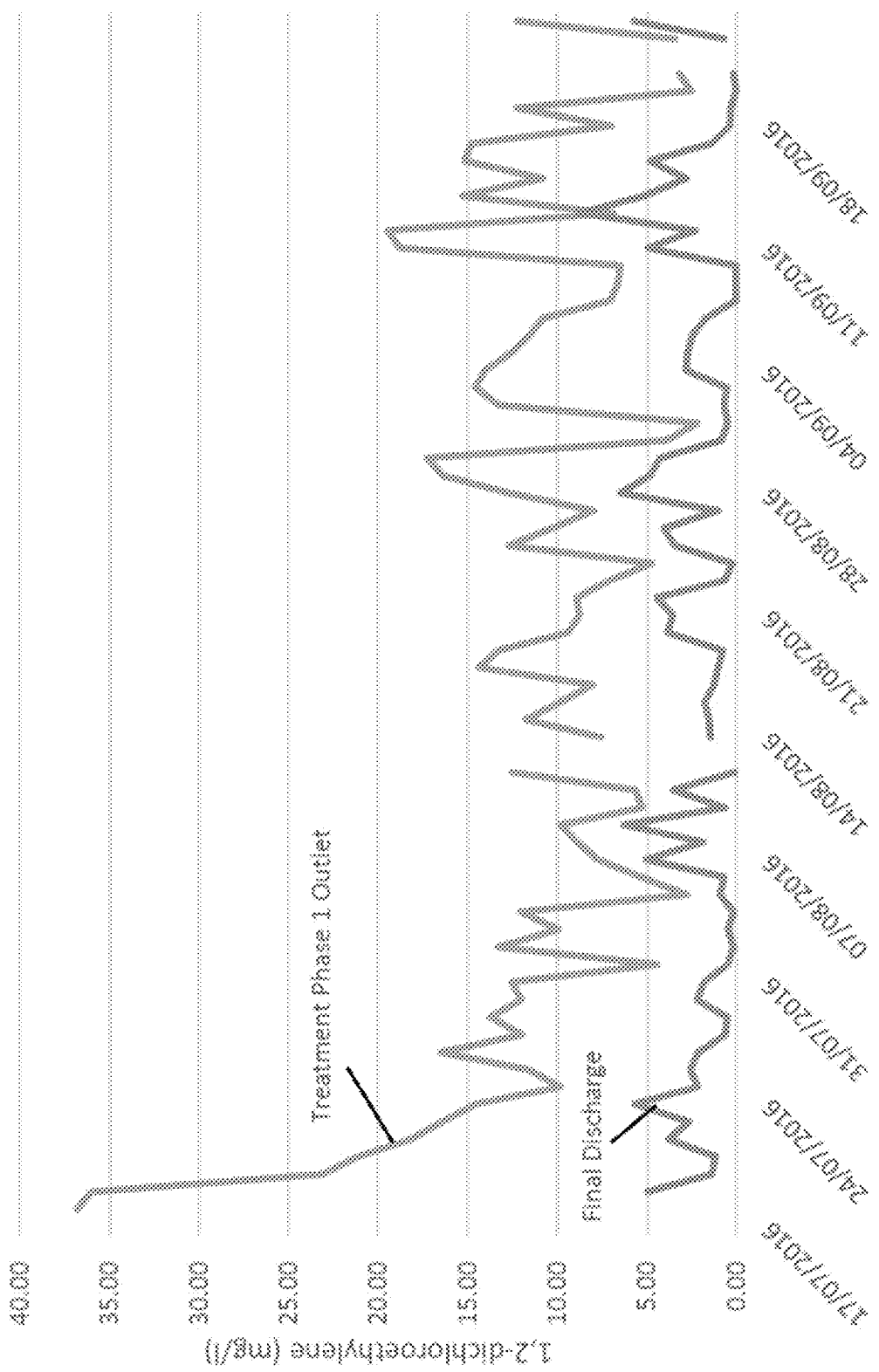
FIG. 6 is a plot of concentrations of 1,2-dichloroethylene vs. time with daily measurements at two different points in the system of FIG. 4, providing evidence of effective breakdown of contaminants.

FIG. 6 shows linear plots comparing the sample analysis results on a reduced Y-axis for the phase 1 treatment outlet and the final discharge outlet.

Figure 7:
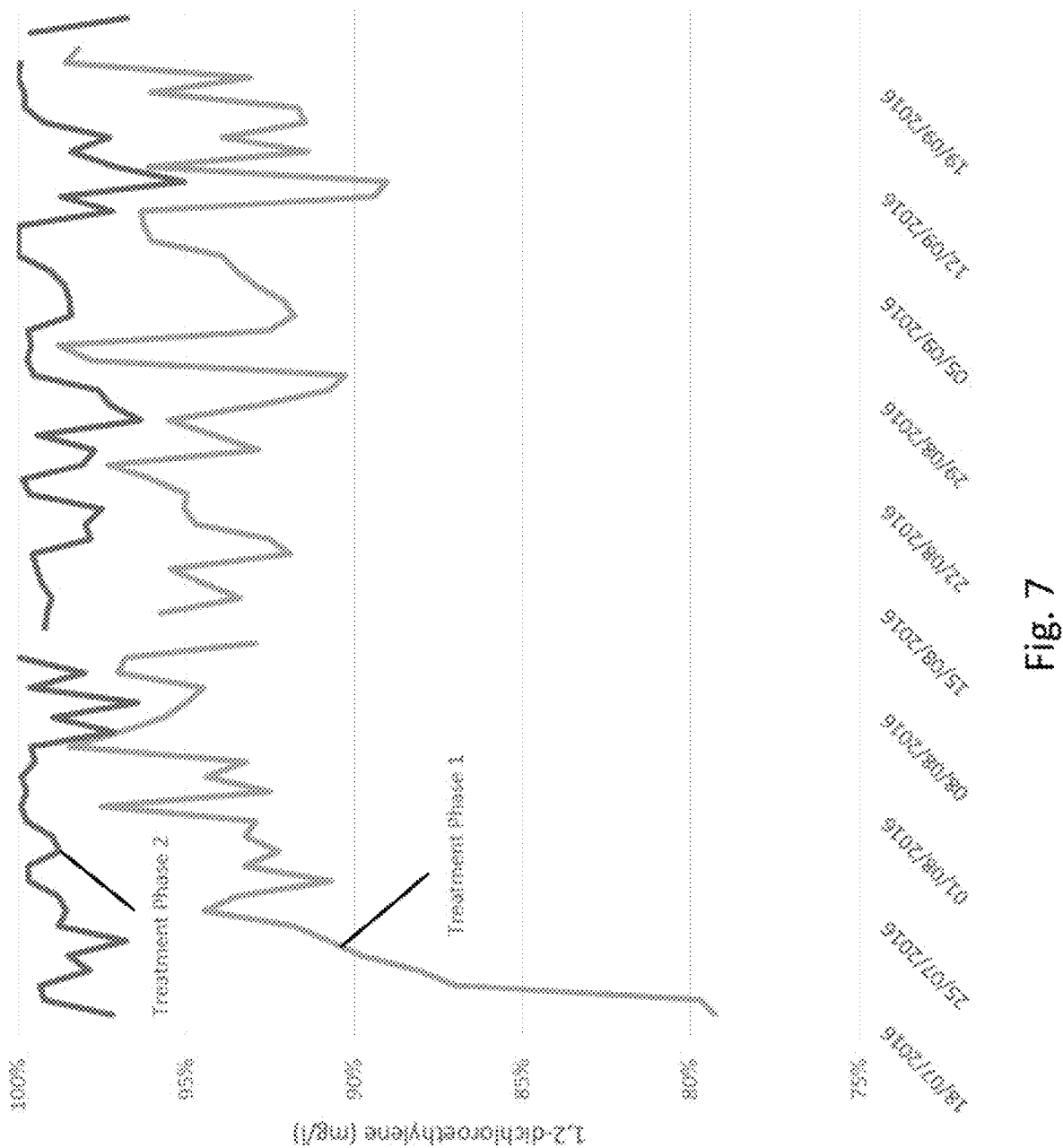
FIG. 7 is a plot of percentage contaminant load reduction through treatment phases 1 and 2.

FIG. 7 shows linear plots indicating percentage containment load reduction through treatment phase 1 and phase 2.

Upon commencing the performance test, contaminant removal through the first phase of treatment began at 79% and over the course of the first 4 days increased to 90%. Contaminant removal through the combined phases 1 and 2 of the treatment system began at 97%, and continued with greater than 95% contaminant removal.

The timeframe results show a distinct improvement when compared to standard soil based reed beds, where system commissioning can be expected to produce a 40-60% reduction in contaminant loading and with greater than 90% contaminant removal only being reached after a 1-4 month period, depending on the contaminant type and load.

The data obtained in this study indicates that using the described methodology, useful microbial populations can be developed on the surfaces of inherently inert media. Conventional soil reed beds, whilst ultimately achieving the same level of treatment via bacterial complexity and population, can take a sustained period of establishment and development to reach the ultimate treatment targets. As such, this period of development is restrictive in project implementation and economics. The study has shown that the described methodology provides an enhancement to rates of microbial population, and as such acceleration of the establishment and development of the treatment.

The process steps described in this example provide accelerated development of microbial populations, therefore ensuring that start up periods for treatment are not protracted and compare favorably with mechanical based systems.

An inherent benefit of the methodology is that the breakdown of contaminants is very broad spectrum, meaning that a wide array of contaminants can be broken down within the same system at the same time. This is a substantial advancement over conventional bioremediation methodologies.

Example 2: Treatment of Soil Contaminated with Pesticides, Emulsifying Oils and Other Chemicals at an Industrial Site The applicant was requested to investigate and propose a methodology for reclamation of land at a former pesticide manufacturing facility. In addition to historic contamination by manufacturing activity, a catastrophic fire had produced widespread contamination from a broad range of pesticides, emulsifying oils and other chemicals. The contamination was spread over a wide area and had penetrated into the aquifer underlying the site.

The statutory authorities required not only a clean up of surface soil within the site but also a strategy for decontamination of the contaminant plume lying below the site in the aquifer.

A total of 4,500 tons of severely contaminated soil was first excavated from the site and decontaminated using thermal desorption. However, a lower lying area of the site was located above the aquifer and excavation below 1.5 m was not allowed for fear that the disturbance would release a high level of contaminants into the aquifer. Instead samples of the soil were removed for initial testing. This contaminated soil was mixed with clean soil to give a series of 0%, 20% and 50% blended soils which were then planted in boxes with *Phragmites australis*. Contaminated water from the site, containing a small population of bacteria, was then used to irrigate the planted boxes for a period of five weeks on a recirculation system.

The concentration of contaminants in the site water was recorded at the start of the trials and then the final concentration after five weeks was recorded. The concentrations were corrected for variation in the soil blends.

The analysis showed quite clearly that the complex chemical mixture was being degraded and simple plate counts of bacteria indicated that greater numbers and varieties of bacteria had developed during the process.

The rhizosphere containing plant roots, soil, and soil microbiology were homogenized and the aqueous extract was fermented to produce a concentrate of the rhizosphere microorganisms. This material was taken back to site and sprayed onto the remaining layers of contaminated soil. The initial sampling of the area showed a variation of between 800 and 1000 mg/kg of total pesticide concentration plus other organic materials. The target required by the Statutory Authorities was less than 10 mg/kg. This target was achieved with final concentrations of 1.82 to 1.95 mg/kg and the decontaminated site was released for construction of a new housing development.

Table 2 provides data indicating percentage reduction of a series of contaminants from soil remediated in the present example.

TABLE 2

Soil Remediation Results after Treating Contaminated Soil with Soil Conditioner

| Parameter Measured (concentration or other indicator Value) | Maximum Indicator Value at Beginning | Maximum Percentage Reduction | Average Percentage Reduction |
| --- | --- | --- | --- |
| ammonia (ppm) | 180 | 100 | 87 |
| anionic detergents (ppm) | 21000 | 93 | 88 |
| chemical oxygen demand (ppm) | 33000 | 95 | 90 |
| color (color units) | 1800 | 74 | 72 |
| oils and grease (ppm) | 120 | 99 | 87 |
| cypermethrin (ppb) | 13 | 100 | 100 |
| diazinon (ppb) | 15 | 100 | 100 |
| dichlofenthion (ppb) | 5 | 100 | 100 |
| dieldrin (ppb) | 1 | 100 | 100 |
| endrin (ppb) | 1.3 | 100 | 98 |
| lindane (ppb) | 1.1 | 100 | 99 |
| mothproofer agent (ppb) | 23 | 100 | 96 |
| p-p'-DDT (ppb) | 5 | 100 | 100 |
| permethrin (ppb) | 118 | 100 | 98 |
| propetamphos (ppb) | 36 | 95 | 78 |
| trans-chlorfenvinphos (ppb) | 9 | 100 | 83 |

This methodology generates a soil conditioner concentrate containing single and co-metabolic systems amongst other species of soil organism and generates results which appear to be more efficient than presently used processes for soil bioremediation.

EQUIVALENTS AND SCOPE

Other than described herein, or unless otherwise expressly specified, all of the numerical ranges, amounts, values and percentages, such as those for amounts of materials, elemental contents, times and temperatures, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Any patent, publication, internet site, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Unless otherwise defined, all technical and scientific terms used herein have the same meaning as commonly understood by one of ordinary skill in the art to which this invention belongs.

While this invention has been particularly shown and described with references to embodiments thereof, it will be understood by those skilled in the art that various changes in form and details may be made therein without departing from the scope of the invention encompassed by the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context.

It is also noted that the term "comprising" is intended to be open and permits but does not require the inclusion of additional elements or steps. When the term "comprising" is used herein, the term "consisting of" is thus also encompassed and disclosed. Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where the term "about" is used, it is understood to reflect +/−10% of the recited value. In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein.

The invention claimed is:

1. A process for preparing a soil conditioner to increase the rate of decontamination of contaminated water or contaminated soil, the process comprising:

a) providing a rhizosphere;
   b) exposing the rhizosphere to the contaminated water;
   c) obtaining a sample of the rhizosphere, the sample comprising plant roots and soil surrounding the rhizome;
   d) extracting microorganisms from the sample after step c) to prepare a microbial extract;
   e) preparing a microbial suspension from the microbial extract; and
   f) subjecting the microbial suspension to growth conditions to increase the concentration of the microorganisms, thereby preparing the soil conditioner, wherein the soil conditioner includes microorganisms originally present in the contaminated water and microorganisms originally present in the rhizosphere.

2. The process of claim 1, wherein step b) comprises generating a flow of the contaminated water across the rhizosphere, the flow entering at an inlet and exiting at an outlet.

3. The process of claim 2, wherein the flow of the contaminated water is conducted for a period of about 4 to about 8 weeks.

4. The process of claim 2, further comprising testing of outflow from the outlet to identify one or more metabolic products of one or more contaminants present in the contaminated water.

5. The process of claim 1, further comprising measuring the amount of microorganisms present in the extract in the microbial suspension.

6. The process of claim 1, further comprising measuring the amount of microorganisms present in the soil conditioner, wherein a plate count of at least about $10^6$ counts/mL indicates that the soil conditioner is suitable for use in treatment of a soil bed in construction of the soil-based flow-through rhizosphere system.

7. The process of claim 1, wherein the rhizosphere is of a wetland plant.

8. The process of claim 7, wherein the wetland plant is selected from the group consisting of *Phragmites australis, Arundo donax* L., *Neyraudia reynaudiana, Phalaris arundinacea, Glyceria maxima, Elegia tectorum, Thamnochortus insignis*, a species of the genus *Calamagrostis*, a species of the genus *Sparganium*, and a species of the genus *Typha*.

9. The process of claim 1, wherein steps a) and b) are conducted in a test bioreactor having a volume of about 10 L to about 50 L.

10. The process of claim 1, wherein the contaminated water comprises organic contaminants.

11. A process for constructing a soil-based rhizosphere flow-through system to break down contaminants in contaminated water, the process comprising:

a) providing plants planted in a test bioreactor, the plants providing a rhizosphere;
   b) exposing the rhizosphere to the contaminated water;
   c) obtaining a sample of the rhizosphere, the sample comprising plant roots and soil surrounding the rhizome;
   d) extracting microorganisms from the sample after step c) to prepare a microbial extract;
   e) preparing a microbial suspension from the microbial extract;
   f) subjecting the microbial suspension to growth conditions to increase the concentration of the microorganisms, thereby preparing a soil conditioner, wherein the soil conditioner includes microorganisms originally present in the contaminated water and microorganisms originally present in the rhizosphere;

g) adding the soil conditioner to different soil in a contained area having a water flow inlet and outlet; and h) planting a plurality of plants in the different soil, the plants being of the same species as the plants of step a).

12. The process of claim 11, wherein step b) comprises generating a flow of the contaminated water across the rhizosphere, the flow entering at an inlet and exiting at an outlet.

13. The process of claim 12, wherein the flow of the contaminated water is conducted for a period of about 4 to about 8 weeks.

14. The process of claim 12, further comprising testing of outflow from the outlet to identify one or more metabolic products of one or more contaminants present in the contaminated water.

15. The process of claim 11, further comprising measuring the amount of microorganisms present in the extract in the microbial suspension.

16. The process of claim 11, further comprising measuring the amount of microorganisms present in the soil conditioner, wherein a plate count of at least about $10^6$ counts/mL indicates that the soil conditioner is suitable for use in treatment of a soil bed in construction of the soil-based flow-through rhizosphere system.

17. The process of claim 11, wherein the rhizosphere is of a wetland plant.

18. The process of claim 17, wherein the wetland plant is selected from the group consisting of *Phragmites australis, Arundo donax* L., *Neyraudia reynaudiana, Phalaris arundinacea, Glyceria maxima, Elegia tectorum, Thamnochortus insignis*, a species of the genus *Calamagrostis*, a species of the genus *Sparganium*, and a species of the genus *Typha*.

19. The process of claim 11, wherein steps a) and b) are conducted in a test bioreactor having a volume of about 10 L to about 50 L.

20. The process of claim 11, wherein the contaminated water comprises organic contaminants.

21. A soil-based flow-through rhizosphere system for breaking down contaminant organic compounds in contaminated water, the system comprising:

a) a contained area comprising soil treated with a soil conditioner prepared according to the process of claim 1 and planted with plants of the same species as the rhizosphere, the contained area having a water flow inlet and a flow outlet;

b) a tank for holding the contaminated water before entry of the contaminated water into the contained area; the tank in flow communication with the flow inlet; and c) a retention pond in communication with the flow outlet.

22. The system of claim 21, further comprising a soakaway discharge pond in flow communication with the retention pond to allow discharge of treated water into the environment.

23. The system of claim 21, further comprising a recirculation line in flow communication between the retention pond and the water flow inlet.

24. The system of claim 21 wherein the contained area is a container configured to provide predominately horizontal flow of the contaminated water from the flow inlet to the flow outlet.

25. The system of claim 24, wherein the container comprises a soil depth of between about 0.4 m to about 0.5 m to provide a predominately aerobic soil environment.

26. The system of claim 21 wherein the contained area is a container configured to provide predominately vertical flow of the contaminated water from the flow inlet to the flow outlet.

27. The system of claim 26, wherein the container comprises a soil depth of between about 0.8 m to about 1.0 m to provide soil having both a predominately aerobic soil environment closer to the soil surface and a predominately anaerobic soil environment closer to the bottom of the container.

* * * * *